US 12,423,818 B2

United States Patent
Huang

(10) Patent No.: US 12,423,818 B2
(45) Date of Patent: Sep. 23, 2025

(54) NON-RESPIRATORY BODY MOVEMENT DETECTION IN RESPIRATORY TRIGGERING

(71) Applicant: Siemens Healthcare GmbH, Erlangen (DE)

(72) Inventor: Yan Tu Huang, Shenzhen (CN)

(73) Assignee: Siemens Healthineers AG, Erlangen (DE)

(*) Notice: Subject to any disclaimer, the term of this patent is extended or adjusted under 35 U.S.C. 154(b) by 838 days.

(21) Appl. No.: 17/576,174

(22) Filed: Jan. 14, 2022

(65) Prior Publication Data

US 2022/0230318 A1 Jul. 21, 2022

(30) Foreign Application Priority Data

Jan. 21, 2021 (CN) .......................... 202110080373.4

(51) Int. Cl.
*A61B 5/05* (2021.01)
*G06T 7/00* (2017.01)
*G06V 40/20* (2022.01)

(52) U.S. Cl.
CPC ............ *G06T 7/0016* (2013.01); *G06V 40/20* (2022.01); *G06T 2207/10088* (2013.01); *G06T 2207/20081* (2013.01); *G06T 2207/30061* (2013.01); *G06V 2201/031* (2022.01)

(58) Field of Classification Search
CPC ......... G06T 7/0016; G06T 2207/10088; G06T 2207/20081; G06T 2207/30061; G06V 40/20
See application file for complete search history.

(56) References Cited

U.S. PATENT DOCUMENTS

| | | |
|---|---|---|
| 2011/0152668 A1 | 6/2011 | Stemmer |
| 2016/0313429 A1 | 10/2016 | Van Den Brink et al. |
| 2016/0367198 A1* | 12/2016 | Chon ................. A61B 5/02416 |
| 2020/0110145 A1 | 4/2020 | Zeller |
| 2020/0333419 A1 | 10/2020 | Zhang et al. |
| 2021/0146158 A1 | 5/2021 | Wirtz et al. |
| 2021/0279891 A1 | 9/2021 | Mysore Siddu et al. |

FOREIGN PATENT DOCUMENTS

| | | |
|---|---|---|
| CN | 111830449 A | 10/2020 |
| JP | 2014161566 A | 9/2014 |
| WO | 2015092062 A1 | 6/2015 |
| WO | 2020011947 A1 | 1/2020 |

\* cited by examiner

*Primary Examiner* — Joel F Brutus
(74) *Attorney, Agent, or Firm* — Banner & Witcoff Ltd.

(57) ABSTRACT

A medical imaging method for detecting a movement and a magnetic resonance imaging system, wherein the method includes: receiving, through a plurality of channels, a plurality of original first time domain signals recording a movement of an object under examination; transforming, based on a plurality of respiratory frequency components as bases, the plurality of first time domain signals into a vector matrix including representations of phases; computing an eigenvector based on the vector matrix; transforming the first time domain signals into second time domain signals based on the eigenvector, and removing a maximum energy term related to a respiratory movement from the second time domain signals; and determining whether a portion of a non-respiratory body movement is detected, and determining to execute a sequence based on only a first time domain signal in which a portion of a non-respiratory body movement is not detected.

13 Claims, 6 Drawing Sheets

NON-RESPIRATORY BODY MOVEMENT DETECTION IN RESPIRATORY TRIGGERING

TECHNICAL FIELD

The present disclosure relates to the field of medical imaging, and in particular to a method for detecting a movement of an imaged object in medical imaging.

BACKGROUND

In a medical imaging process, a final medical image has blurs and artifacts due to a movement of an object under examination in a photographing process, causing reduction in image quality. Such reduction in image quality leads to incorrect diagnosis during film reading, repeated scanning, etc., causing reduction in medical image acquisition efficiency and an increase in costs.

A magnetic resonance imaging (MRI) system is taken as an example, which is a medical imaging technology that irradiates an object with a radio frequency pulse signal by using an antenna in a certain magnetic field condition and performs imaging based on a modulated radio frequency signal received from the object. The magnetic resonance imaging technology can be used to study the internal structure, material composition, physiological process, etc. of the object. A radio frequency pulse with a Larmor frequency causes spin nuclei, such as hydrogen nuclei (that is, H+), in the object subjected to the irradiation to undergo the precession with a deflection angle. After excitation, a magnetic resonance radio frequency signal is generated, which is received by using a receiving coil/antenna, and processed by using a computer for imaging.

In the magnetic resonance imaging system, image acquisition requires several milliseconds to several minutes depending on a pulse sequence (also referred to as a sequence) used. It is therefore meaningful to start the image acquisition correspondingly when the body is kept stationary, in order to avoid artifacts caused by movements during the image acquisition. However, some irregular body movements lead to motion artifacts that blur an acquired image. Inevitable movements include respiration, heartbeat, etc. However, a calm phase follows the movement phase, for example, after expiration or myocardial contraction. The image acquisition in this phase which may be a relatively long phase with few movements may be expected to result in the best measurement result.

In addition, movement information is acquired by means of reference radio frequency signals such as some high-frequency signals or radio frequency signals. Here, data or information related to a patient's mechanical movements can be read by using some modulation and decoding methods, so as to identify the patient's movements caused by respiration, heartbeat, etc.

Certainly, in addition to magnetic resonance imaging, the problems described above are also found in, for example, imaging in computed tomography (CT), positron emission tomography (PET), single-photon emission computed tomography (SPECT), etc.

SUMMARY

In view of the above, one aspect of the present disclosure provides a medical imaging method for detecting a movement, to detect interference from a movement other than mechanical physiological movements, including a body movement of an object under examination, etc., to eliminate an image blur and/or artifact introduced by an irregular movement in a medical imaging process. The method for detecting a movement of an object in medical imaging includes: receiving, through a plurality of channels, a plurality of original first time domain signals recording a movement of the object under examination; transforming the plurality of first time domain signals based on a plurality of respiratory frequency components as bases, to obtain a vector matrix including representations of phases; computing an eigenvector based on the vector matrix including the representations of the phases; transforming the first time domain signals into second time domain signals based on the eigenvector, removing at least one maximum energy term related to a respiratory movement from the second time domain signals, and determining whether a portion of a non-respiratory body movement in the second time domain signals is detected; and determining, after the portion of the non-respiratory body movement is detected, whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement.

Optionally, the removal of at least one maximum energy term related to a respiratory movement from the second time domain signals, and determining whether a portion of a non-respiratory body movement in the second time domain signals is detected includes: removing at least one maximum energy term from the second time domain signals, to obtain third time domain signals; dividing the third time domain signals up based on different sub-time periods, and computing a correlation coefficient between the third time domain signals in the sub-time periods; and determining, based on a comparison between the correlation coefficient and an a priori threshold, whether a portion of a non-respiratory body movement in the third time domain signals is detected.

Optionally, the reception, through a plurality of channels, of a plurality of original first time domain signals recording a movement of the object under examination includes: receiving, from a plurality of coil units through the plurality of channels, the plurality of first time domain signals recording the movement of the object under examination, the first time domain signals including pilot tone signals or navigation echo signals.

Optionally, the reception, through a plurality of channels, of a plurality of original first time domain signals recording a movement of the object under examination includes: sampling, based on a sampling frequency in a time period, the plurality of first time domain signals to construct discrete representations of the first time domain signals.

Optionally, the transformation, based on a plurality of respiratory frequency components as bases, of the plurality of first time domain signals into a vector matrix including representations of phases includes: dividing based on an a priori respiratory frequency range, a sampling frequency, and a time period for acquiring the plurality of first time domain signals, to obtain the plurality of respiratory frequency components; constructing a filter based on phases of the plurality of respiratory frequency components; and transforming, based on the filter, the first time domain signals into the vector matrix including the representations of the phases.

Optionally, the computing of an eigenvector based on the vector matrix including the representations of the phases includes: computing the eigenvector through eigendecomposition and based on the vector matrix represented by using the respiratory frequency components.

Another aspect of the present disclosure provides a magnetic resonance imaging system for providing an image representation of an object of interest positioned in an examination space of the magnetic resonance imaging system, where the magnetic resonance imaging system is adapted to perform the foregoing medical imaging method for detecting a movement.

Another aspect of the present disclosure provides an electronic device, including: a processor; and a memory storing a program, the program including instructions that, when executed by the processor, cause the processor to perform the foregoing medical imaging method for detecting a movement.

Another aspect of the present disclosure provides a computer-readable storage medium, a program including instructions that, when executed by a processor of an electronic device, cause the electronic device to perform the foregoing medical imaging method for detecting a movement.

Another aspect of the present disclosure provides a system for detecting a movement of an object under examination in medical imaging, where the system includes: an interface portion configured to receive, through a plurality of channels, a plurality of original first time domain signals recording a movement of an object under examination; a filter configured to transform, based on a plurality of respiratory frequency components as bases, the plurality of first time domain signals into a vector matrix including representations of phases; an eigenvector computing portion configured to compute an eigenvector based on the vector matrix including the representations of the phases; and a movement determination portion configured to transform the first time domain signals into second time domain signals represented in a respiratory frequency space based on computation of the eigenvector, remove at least one maximum energy term related to a respiratory frequency from the second time domain signals to obtain third time domain signals, and compute a correlation between the third time domain signals in the sub-time periods, to determine whether a portion of a non-respiratory body movement in the third time domain signals is detected.

Optionally, the filter is configured to divide based on an a priori respiratory frequency range, a sampling frequency, and a time period for acquiring the plurality of first time domain signals, to obtain the plurality of respiratory frequency components. The filter is configured to be constructed based on phases of the plurality of respiratory frequency components. The filter is further configured to transform the first time domain signals into the vector matrix including the representations of the phases.

Optionally, the movement determination portion of the system is further configured to divide the third time domain signals up based on different sub-time periods, compute a correlation coefficient between the third time domain signals in the sub-time periods, and determine, based on a comparison between the correlation coefficient and an a priori threshold, whether a portion of a non-respiratory body movement in the third time domain signals is detected.

Optionally, the movement determination portion is further configured to give feedback to a control unit as to whether the portion of the non-respiratory body movement in the third time domain signals is detected. The control unit is configured to determine, after receiving feedback that the portion of the non-respiratory body movement is detected, whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement.

The medical imaging method for detecting a movement provided by the present disclosure has the following advantages:

1. It is possible to further detect an irregular body movement of the object under examination, for example, the non-respiratory body movement, to abort execution of a sequence when the non-respiratory body movement is detected. Therefore, the execution using, for example, a respiratory movement signal or curve as a sequence is optimized to trigger the acquisition, post-processing, etc. of the magnetic resonance signal, including triggering or gating of execution of the sequence, etc.; particularly, an indicator for execution using a pilot tone as a sequence is optimized, thereby effectively eliminating image artifacts or blurs after imaging caused by the non-respiratory body movement, and optimizing image acquisition efficiency.
2. The medical imaging method for detecting a movement provided by the present disclosure makes it possible to detect, based on a self-gating concept, the portion of the non-respiratory body movement in the originally acquired first time domain signal, so as to continuously acquire signals.
3. The filter constructed based on an a priori respiratory frequency is provided. The filter may transform the time domain signals acquired through the plurality of channels into a frequency domain to obtain the vector matrix including the representations of the phases, and obtain the eigenvector for the respiratory frequency-related components through eigendecomposition computation and based on the vector matrix. Therefore, the originally acquired first time domain signals are transformed into the second time domain signals described in the respiratory frequency space. The filter uses a difference, in the respiratory frequency space, between a vector of movement components and a vector related to a respiratory movement, to effectively distinguish an eigenvector of a movement-related component to obtain time domain signals of the movement components. The method or model has high robustness, that is, after a correlation coefficient of similarity or correlation between the time domain signals of the movement components in the sub-time periods is computed, the non-respiratory body movement is further effectively identified or distinguished from some irregular mechanical physiological movements, especially interference signals from irregular respiration, including deep/shallow respiration, breath holding, etc.
4. The first time domain signals are transformed based on the computed eigenvector of the respiratory frequency-related components into the second time domain signals characterized in the respiratory frequency space. At least one maximum energy term is removed to obtain the third time domain signals without the respiratory frequency-related components. The third time domain signals include only a signal independent of the respiratory movement, thereby further detecting, based on the third time domain signals, some irregular mechanical physiological movements, especially the body movement against interference signals and having high robustness.

5. The constructed filter may be rapidly configured to identify the non-respiratory body movement in the originally acquired first time domain signals, and abort executing or execute, based on the non-respiratory body movement as an indicator, a sequence for the originally acquired first time domain signals in near real time, specifically including determining whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement.

6. The plurality of time domain signals recording the movement of the object under examination are acquired through the plurality of channels. The matrix for the plurality of time domain signals is constructed through sampling with a certain frequency. The filter for the frequency domain is further constructed based on dividing based on the sampling frequency and the respiratory frequency, so as to obtain a computable discrete model. Therefore, the accurate eigenvector is further computed to effectively identify the non-respiratory body movement and the mechanical physiological movements including respiration. The method has suitable computability and simple model construction.

BRIEF DESCRIPTION OF THE DRAWINGS

The above and other features and advantages of the present disclosure will become more apparent to those of ordinary skill in the art from the detailed description of the aspects of the present disclosure with reference to the accompanying drawings. In the accompanying drawings.

Figure 1:
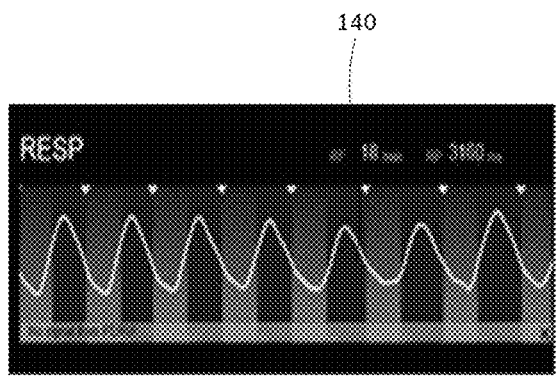
FIG. 1 is a magnetic resonance imaging picture of a region of interest taken under a respiratory movement according to an exemplary aspect.
Figure 1:
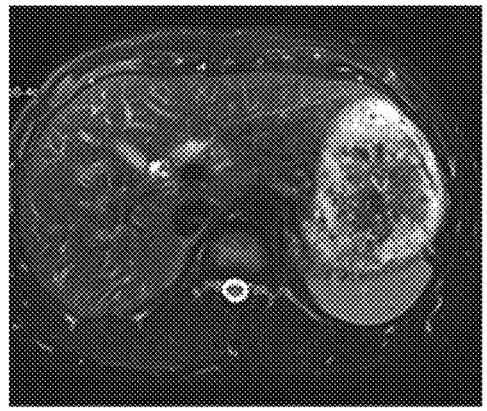

Reference numerals in the accompanying drawings are as follows:
- 100 Magnetic resonance imaging system
- 102 Magnet
- 104 Gradient coil
- 106 Radio frequency coil
- 108 Examination region
- 110 Gradient transmission unit
- 112 Radio frequency unit
- 114 Radio frequency switching unit
- 116 Pilot tone transmitter
- 118 Pilot tone receiver
- 120 Local coil
- 122 Region of interest
- 126 Control unit
- 1261 Movement detection system
- 1262 Interface portion
- 1264 Filter
- 1266 Eigenvector computing portion
- 1268 Movement determination portion
- 128 Display unit
- 130 Image reconstruction unit
- 132 First window
- 134 Second window
- 136 Portion of non-respiratory body movement
- 140 Curve of respiratory movement signal
- 142 Curve of respiratory movement signal affected by non-respiratory body movement
- P Object under examination

DETAILED DESCRIPTION

For a clearer understanding of the technical features, objectives, and effects of the present disclosure, the specific aspects of the present disclosure will now be described with reference to the accompanying drawings, where the same reference numerals represent the same parts.

The word "exemplary" represents "serving as an instance, example, or description" herein, and any illustration and implementation described as "exemplary" herein should not be interpreted as a more preferred or more advantageous technical solution.

In order to simplify the drawings, only the parts related to the present disclosure are schematically shown in each drawing, and they do not represent the actual structure of the product. In addition, in order to make the drawings concise and easy to understand, in some drawings, only one of the components having the same structure or function is schematically shown or only one of them is marked.

Herein, "a/an" means not only "only one", but also "more than one". Herein, "first", "second", etc. are only used to distinguish one item from another, and do not indicate their importance and order, the premise for mutual existence, etc. Further, the term "and/or" used in the present disclosure encompasses any one of and all possible combinations of the listed items. For example, A and/or B may represent the following three cases: only A exists, both A and B exist, and only B exists. In addition, the character "/" herein generally indicates an "or" relationship between the associated objects.

In a magnetic resonance tomography system, to ensure that magnetic resonance image acquisition is triggered during breath holding, to reduce a motion artifact introduced by a respiratory movement, etc., a pilot tone is exemplarily used for detecting movement signals including respiration, etc. The pilot tone may use signals acquired through a plurality of channels as a leading indicator for executing a sequence, for example, triggering the sequence or implementing gating, including setting one or more time points for triggering image acquisition, post-processing an acquired image, or setting gating of the acquired image. For example, the triggering of the sequence is intended to set, based on a curve or phase information of respiratory movement signals, triggering of a sequence for acquiring a magnetic resonance signal of a region of interest, or set, based on the curve or phase information, a trigger point or condition for receiving the magnetic resonance signal from the region of interest. The post-processing of an acquired magnetic resonance signal includes triggering related k-space data for imaging etc. The gating is intended to set a window range based on a respiratory movement curve for signal acquisition. In addition, the gating further includes, for example, prospective gating, retrospective gating, etc.

Figure 2:
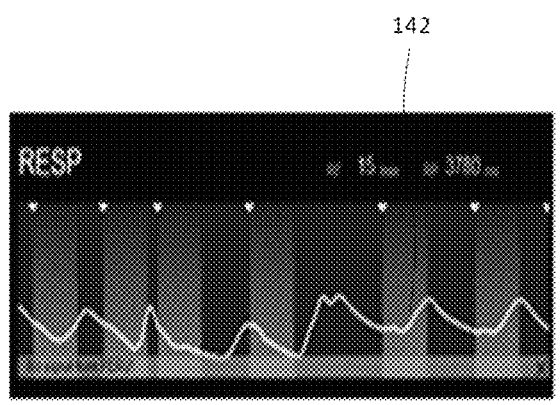
FIG. 2 is a magnetic resonance imaging picture of a region of interest taken under interference from a non-respiratory body movement according to an exemplary aspect.
Figure 2:
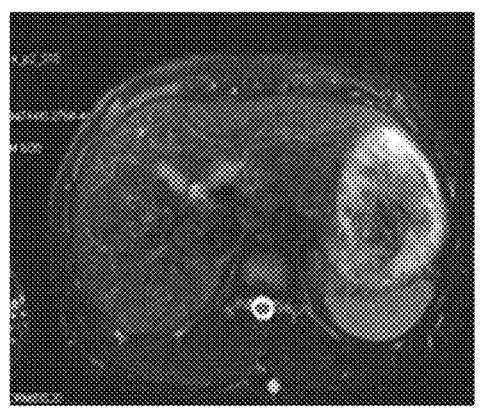

The pilot tone has obvious advantages, such as there being no need to improve image quality through breath holding when an image of an object under examination is acquired. However, when a pilot tone signal is analyzed, even if a respiratory signal can be detected, the respiratory signal is still affected by irregular movements including a body movement, etc. Therefore, accuracy of an algorithm or a method for triggering acquisition of the magnetic resonance signal based on a waveform setting of the respiratory signal is affected, resulting in an image artifact or blur. With reference to FIGS. 1 and 2, FIG. 1 shows a curve 140 of a respiratory movement signal obtained after pilot tone signals from a plurality of channels are combined. An image obtained by determining to execute a sequence based on the curve has a desirable quality. The curve 140 of the respiratory movement signal is not affected or interfered with by a non-respiratory body movement. FIG. 2 shows a curve 142 of a respiratory movement signal that is affected by a non-respiratory body movement. Under the impact of irregular movements including a body movement of an object P under examination, etc., an image obtained through execution of a sequence based on the curve has a significant artifact or blur.

The present disclosure provides a magnetic resonance imaging method. The method is based on detecting a non-respiratory body movement, for example, detecting a portion of the non-respiratory body movement in a pilot tone signal or a navigation echo signal. It is a challenge to simultaneously reduce impact from respiratory movements including deep/shallow respiration, irregular respiration, etc., to further distinguish a body movement from movements introduced by the deep/shallow respiration or the irregular respiration. In general, a vector of a body movement signal and a vector of a respiratory movement signal have different characteristics. Therefore, in the present disclosure, the body movement can be detected by separating the body movement signal from the respiratory movement signal.

Figure 3:
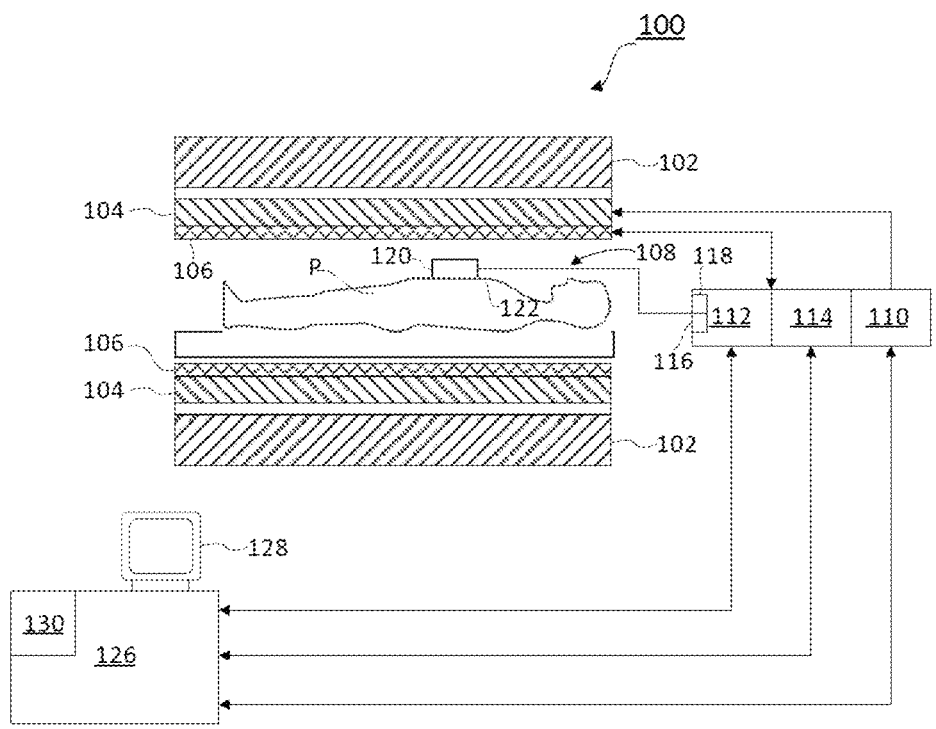
FIG. 3 is a schematic diagram of a structure of a magnetic resonance imaging system including a pilot tone transmitter and a pilot tone receiver according to an exemplary aspect.

FIG. 3 is a schematic diagram showing a magnetic resonance imaging system according to the present disclosure that includes a pilot tone transmitter and a pilot tone receiver according to an exemplary aspect.

As shown in FIG. 3, the magnetic resonance imaging system 100 includes: a magnet 102, the magnet 102 providing a uniform static magnetic field $B_0$ in an examination region 108, for aligning a nuclear spin of an object or a patient under measurement. In particular, uniformity of the static magnetic field $B_0$ relates to strength or magnitude of the magnetic field. The magnet 102 is provided with a central cavity that is provided to surround the examination region 108 for the object P under examination to be positioned therein. In addition, the object P under examination may be moved by a mobile unit (not shown) arranged in a channel of the examination region 108. The magnet 102 is generally a superconducting magnet that may provide a magnetic field having a magnetic flux density of 0.55 T, 1.5 T, 3.0 T, etc., or even higher if it has not been used beforehand. For a low field strength, however, a permanent magnet or an electromagnet with a normally conductive coil may also be used.

In addition, the magnetic resonance imaging system 100 is further provided with a gradient coil 104, the gradient coil 104 being configured to generate a gradient magnetic field superimposed on the magnetic field $B_0$, and the gradient magnetic field being variable in three spatial directions, for spatially differentiating an imaging region in an examination volume for acquisition. The gradient coil 104 is generally a coil made of a normally conductive metal wire that may generate fields orthogonal to one another in the examination volume. A gradient transmission unit 110 may be configured to receive, from a control unit 126, a set of pulse sequences related to a gradient field, for supplying a variable current to the gradient coil 104 via a feeder line, the variable current providing a desirable gradient field in the examination volume in a time-coordinated manner.

In addition, the magnetic resonance imaging system 100 is further provided with a radio frequency coil 106, also known as a body coil, the radio frequency coil 106 being capable of being designed as a tubular or cylindrical integral coil. The radio frequency transmitting coil 106 is configured to radiate, into the examination region 108 in a radio frequency (RF) transmitting phase, a radio frequency signal fed via a signal conductor to excite nuclei of the object P under examination. The radio frequency coil 106 also receives magnetic resonance signals from excited nuclei in an RF receiving phase and transmits same via a signal conductor. Upon the operation of the control unit 126, an RF transmitting phase and an RF receiving phase may occur successively. The gradient coil 104 is coaxially arranged in the cavity of the magnet 102.

In addition, the magnetic resonance imaging system 100 includes: an image reconstruction unit 130 configured to reconstruct a magnetic resonance image based on an acquired magnetic resonance (MR) signal, for example, k-space data; and the control unit 126 provided with a display unit 128 configured to control a magnetic resonance scanning function. A radio frequency unit 112 is configured to feed RF power of a magnetic resonance radio frequency to the radio frequency coil 106 via a radio frequency switching unit 114 in the RF transmitting phase. The radio frequency switching unit 114 may also be controlled by the control unit 126. In the RF receiving phase, after pre-amplification, the radio frequency switching unit 114 feeds the magnetic resonance signal to the image reconstruction unit 130 from the radio frequency coil 106.

In addition, a local coil 120 may be arranged at a proximal end of the object P under examination, in particular, in a region of interest 122, for example, a chest. The local coil 120 may be connected to the radio frequency unit 112 through a connection line and thus be configured to transmit, through a radio frequency signal provided by the radio frequency unit 112, an RF magnetic field to the region of interest 122 in the RF transmitting phase, to excite nuclei of the region of interest 122, and receive magnetic resonance signals of excited nuclei of the region of interest 122 through the local coil 120 in the RF receiving phase. After pre-amplification, the radio frequency switching unit 114 transmits the magnetic resonance signals to the image reconstruction unit 130 from the local coil 120.

In addition, the magnetic resonance imaging system 100 includes: a receiver (not shown) including a receiving coil channel selector that may output the magnetic resonance signals to corresponding channels, to form a plurality of channels. The receiver may convert an analog signal into a digital signal and then output same to the control unit 126 for processing. The image reconstruction unit 130 may at least use an inverse Fourier transform operation to reconstruct, from the magnetic resonance signal, a spatially differential image about a substance and reflecting an anatomical tissue of the object P under examination. The display unit 128 may display and play a reconstructed image or video.

A radio frequency transmitting portion of the radio frequency unit 112 further includes: a pilot tone transmitter 116. The pilot tone transmitter 116 can be connected to the local coil 120 or arranged around the local coil 120, or the local coil 120 is provided with a separate transmitting antenna for transmitting a pilot tone signal, or the pilot tone transmitter is arranged next to the magnet 102. In addition, it is also conceivable to arrange a separate transmitting antenna for a pilot tone signal in the examination region 108 or at some regions of interest 122 of the object P under examination. Based on some applications and technical advantages, the pilot tone transmitter 116 may be arranged in the local coil 120.

A receiving portion of the radio frequency unit 120 may include a pilot tone receiver 118. The pilot tone receiver 118 may be in signal connection to the local coil 120, and the local coil 120 may be provided with a receiving antenna for receiving a pilot tone signal. In addition, a receiving antenna for receiving a pilot tone signal is arranged in the examination region 108 or at one region of interest 122 of the object P under examination. For example, it may be an induction loop coil that is used as a receiving antenna and arranged in a decoupled manner with respect to an antenna of an adjacent local coil 120. In some aspects, the pilot tone receiver 118 may be configured as one or more antenna coils of the local coil 120 for receiving magnetic resonance signals, so as to, for example, filter out signals in an MR signal frequency range by performing analog-to-digital (A/D) conversion on original signals acquired by the local coil 120. The pilot tone receiver 118 may be connected to a receiver for receiving a magnetic resonance signal, or use one or more channels of the foregoing receiving coil channel selector to receive a pilot tone signal. The pilot tone receiver 118 may apply a filter or some additional processing steps in the form of an algorithm only to a signal of an antenna coil, to extract a pilot tone signal. In addition, based on some applications and technical advantages, the pilot tone receiver 118 may be arranged in the local coil.

The pilot tone transmitter 116 generates a pilot tone signal, which may be incident, via an induction loop/antenna, on the region of interest 122 of the object P under examination, to sense mechanical physiological movements of the object P under examination, including respiration, heartbeat, etc., as an indicator for triggering a sequence of transmitting a radio frequency signal, thereby reducing an artifact introduced by the mechanical physiological movement. The pilot tone transmitter 116 may be provided with a separate oscillator that may generate a high-frequency signal having a suitable frequency. In some aspects shown, when a frequency is preferably a Larmor frequency used by the magnetic resonance imaging system 100 during imaging or within a frequency range near the Larmor frequency, the oscillator in the pilot tone transmitter 116 may be replaced. An oscillator in the radio frequency unit 112 feeds a radio frequency signal, or the radio frequency signal is generated based on a fed signal in the pilot tone transmitter 116, to maintain stability of the pilot tone signal while acquiring a magnetic resonance signal.

Figure 4:
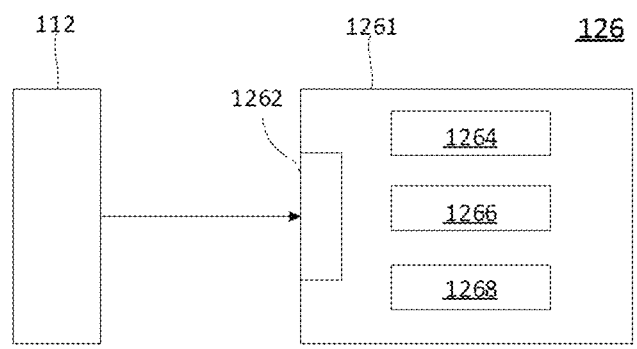
FIG. 4 is a schematic functional diagram of a system for detecting a movement of an object under examination in medical imaging according to an exemplary aspect.

Referring now to FIG. 4, the present disclosure shows a movement detection system 1261 for detecting a movement of an object under examination in medical imaging. The movement detection system 1261 includes: an interface portion 1262 configured to receive, for example, through a plurality of channels of the radio frequency unit 112 in an RF receiving phase, a plurality of original first time domain signals recording a movement of an object under examination; a filter 1264 configured to transform, based on a plurality of respiratory frequency components as bases, the plurality of first time domain signals into a vector matrix including representations of phases; an eigenvector computing portion 1266 configured to compute an eigenvector based on the vector matrix including the representations of the phases; and a movement determination portion 1268 configured to transform the first time domain signals into second time domain signals based on computation of the eigenvector, remove at least one maximum energy term related to a respiratory frequency from the second time domain signals to obtain third time domain signals, and compute a correlation between the third time domain signals in the sub-time periods, to detect a portion of a non-respiratory body movement in the third time domain signals. The second time domain signals represented in a respiratory frequency space are equivalent to a scaled portion, in the first time domain signals, related to the respiratory frequency or the respiratory movement. Therefore, components related to the respiratory movement may be identified from the second time domain signals, that is, the maximum energy term in the second time domain signals is determined, which has the greatest correlation with the respiratory movement. One or more maximum energy terms are removed from the second time domain signals to obtain the third time domain signals which are unrelated to the respiratory movement. The third time domain signals may include signals representative of, for example, a non-respiratory body movement, a heartbeat movement, etc.

In addition, the filter 1264 is configured to divide based on an a priori respiratory frequency range, a sampling frequency, and a time period for acquiring the plurality of first time domain signals, to obtain the plurality of respiratory frequency components. The filter 1264 is configured to be constructed based on phases of the plurality of respiratory frequency components. The filter 1264 is further configured to transform the first time domain signals into the vector matrix including the representations of the phases. Here, the filter 1264 may be implemented by constructing a filter circuit or through a signal processing algorithm.

In addition, the movement determination portion 1268 is further configured to divide the obtained third time domain signals related to non-respiratory movement components up based on different sub-time periods, to obtain a number of sub-time periods or a plurality of time windows, compute a correlation coefficient between the time domain signals in the sub-time periods, and determine, based on a comparison between the correlation coefficient and an a priori threshold, whether a portion of the non-respiratory body movement in the time domain signals is detected. For example, when the correlation coefficient is less than the threshold, it is determined that the portion of the non-respiratory body movement in a sub-time period of the third time domain signals is detected.

In addition, the movement determination portion 1268 may be further configured to give feedback to a control unit 126 as to whether the portion of the non-respiratory body movement in the third time domain signals is detected. When the control unit 126 receives feedback that the portion of the non-respiratory body movement is detected, the control unit 126 is configured to abort execution of the sequence, including determining whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement, etc.

Figure 5:
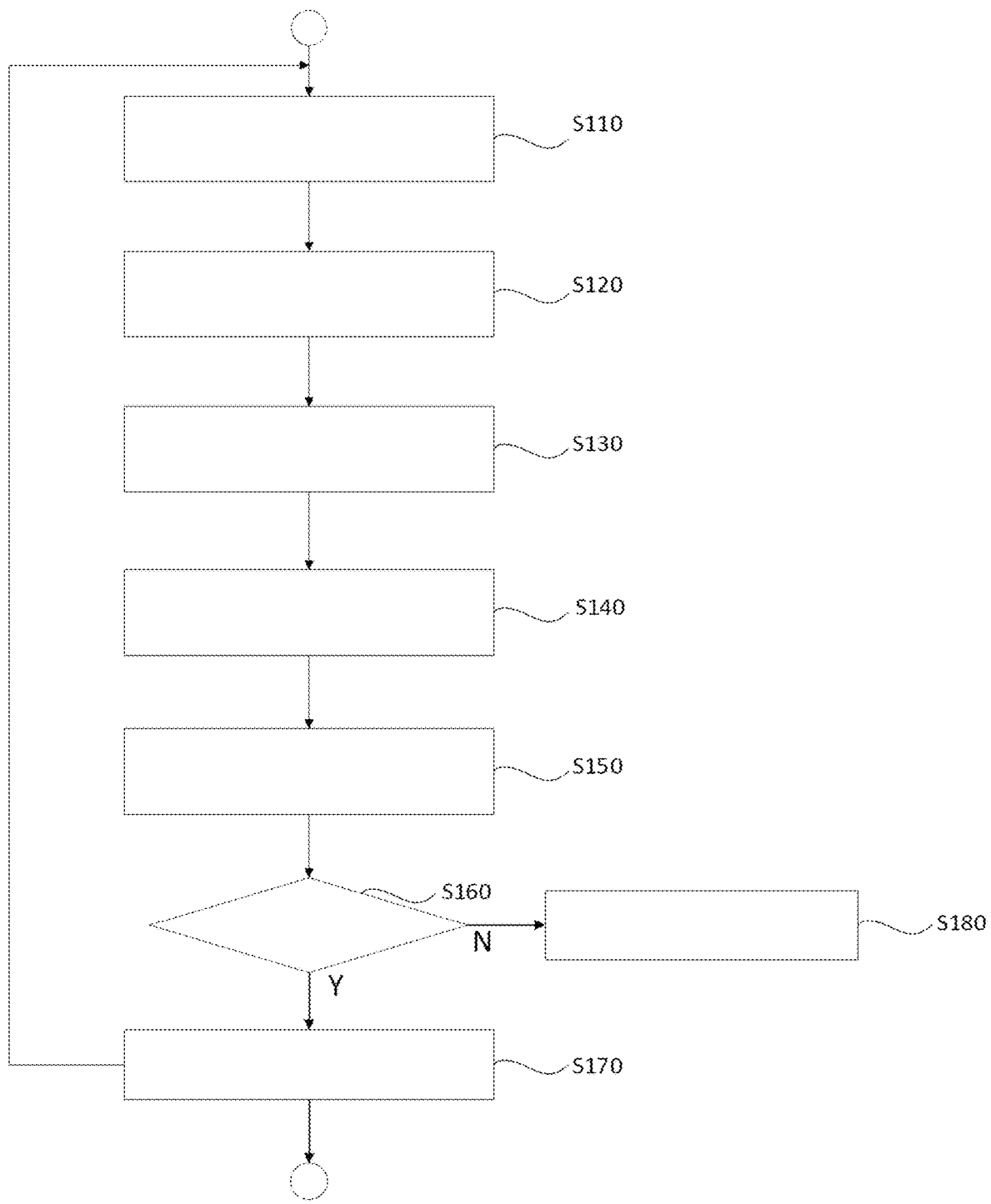
FIG. 5 is a flow chart of a medical imaging method for detecting a movement according to an exemplary aspect.

FIG. 5 is a flow chart of a medical imaging method for detecting a movement that is based on the magnetic resonance imaging system 100. In the method, the pilot tone transmitter 116 is used to transmit a certain high-frequency signal to a region of interest 122 to detect a movement signal of an object P under examination, and a high-frequency signal returned from the region of interest 122 is received at a receiver end through a plurality of channels. Movement signals contained in the returned high-frequency signal may include a respiratory signal related to respiration or/and a heartbeat signal related to heartbeat, and movement signals unrelated to the mechanical physiological movement described above, including a non-respiratory signal related to a body movement of the object under examination, etc. In the method, the mechanical physiological movement can be distinguished from an irregular non-mechanical physiological movement, that is, a common body movement, so as to more accurately detect the movement of the object under examination, and a type of a detected movement is used as an indicator for triggering, for example, a sequence for acquiring an MR signal, so as to reduce an image artifact and blur under the impact from the non-mechanical physiological movement in a magnetic resonance imaging process.

In step S110, a plurality of original first time domain signals recording a movement of an object P under examination are received through a plurality of channels.

Figure 7:
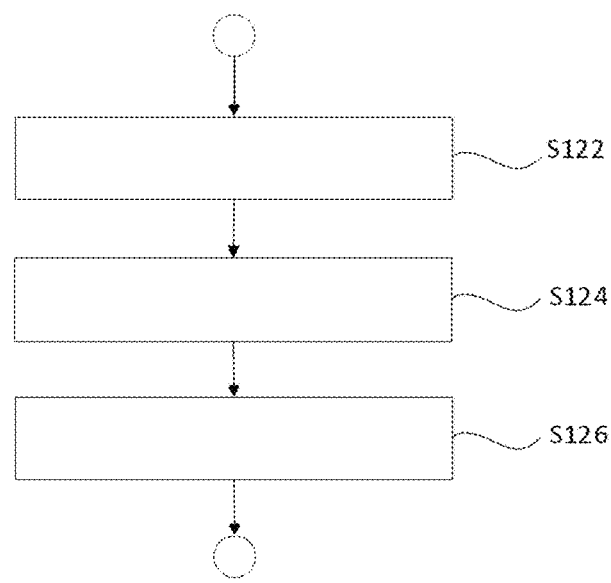
FIG. 7 is a flow chart of a method for constructing a filter that transforms first time domain signals into a frequency domain space related to a respiratory frequency according to an exemplary aspect.
Figure 8:
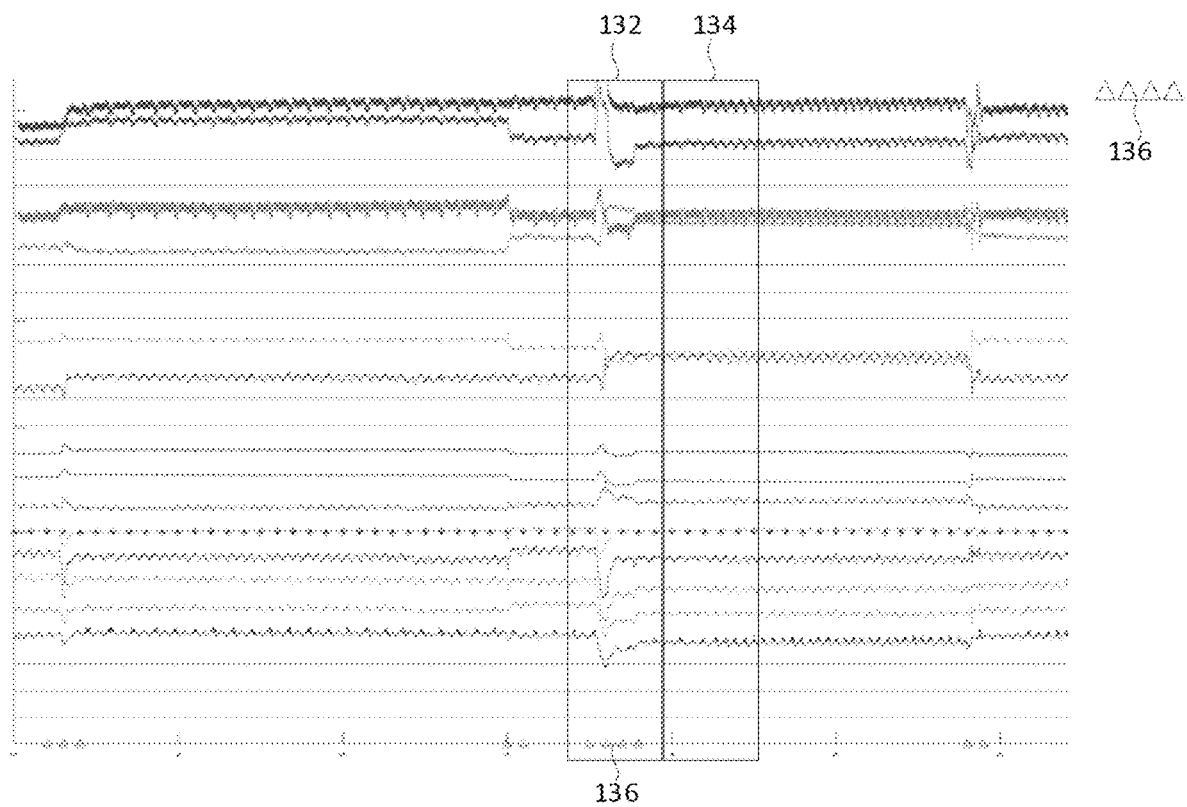
FIG. 8 is a schematic diagram of a time domain signal in which a non-respiratory body movement is detected in pilot tone signals from a plurality of channels according to an exemplary aspect.

For example, in a shown magnetic resonance imaging system 100, a plurality of original first time domain signals recording a related movement of a region of interest 122 of the object P under examination are received through a plurality of channels of a receiver or the pilot tone receiver 118 from a plurality of coil units of the local coil 120, etc., the first time domain signals including a pilot tone signal S(t). The pilot tone transmitter 116 may use a plurality of induction loop coils arranged at the local coil 120 to transmit the high-frequency signal described above to the region of interest 122 of the object P under examination. The pilot tone receiver 118 receives a high-frequency signal returned from the region of interest 122. A plurality of pilot tone signals recording the movement of the object P under examination are received through the plurality of channels at the receiver. Referring to FIGS. 7 and 8, pilot tone signals S(t) from 24 channels are shown, the pilot tone signals S(t) may be expressed as pilot tone signals from a plurality of channels. For example, regarding the pilot tone signals from the 24 channels, S(t) may also be expressed as $[S(t)_1, \ldots, S(t)_{24}]$. The first time domain signals are originally acquired signals and may include a respiratory signal, a heartbeat signal, a signal related to a non-respiratory body movement of the object P under examination, etc.

It should be noted that in addition to the pilot tone, the method or apparatus for receiving the first time domain signals or the time domain signals recording the movement of the object P under examination is also used to, for example, detect a diaphragm movement to identify a navigation echo signal of a respiratory movement, uses an optical sensor or an ultrasonic sensor to detect the mechanical physiological movement of the object P under examination, or provide a respiratory zone to provide mechanical physiological signals from the plurality of channels that reflect the region of interest of the object P under examination. In the present disclosure, there is no limitation on the methods and techniques using the plurality of channels to receive the original time domain signals recording the movement of the object under examination.

In step S120, the plurality of first time domain signals are transformed into a vector matrix including representations of phases based on phases of a plurality of respiratory frequency components. Here, a respiratory frequency range may be a priori. By dividing the respiratory frequency in the range, the plurality of respiratory frequency components and corresponding phase representations may be obtained.

In a shown aspect, specifically, referring to FIG. 7, a method for constructing, based on the a priori respiratory frequency range, a filter which transforms first time domain signals into a frequency domain space related to a respiratory frequency may be as follows:

For example, the first time domain signals include pilot tone signals S(t), the respiratory frequency range usually changes slowly with time, and it is assumed that the respiratory frequency range is $[F_{min}, F_{max}]$.

In step S122, a respiratory frequency is divided based on the a priori respiratory frequency range, a sampling frequency, and a time period for acquiring the first time domain signals S(t), to obtain the plurality of respiratory frequency components.

Here, the pilot tone signals S(t) are separately sampled in a time period T to obtain a matrix R represented by a set of vectors, $R=[S(t_0); S(t_1); \ldots; S(t_{T*N})]$. The pilot tone signals S(t) are discretized, where a range of the time period T is $[t_0, t_T]$, and the sampling frequency is $\Delta f = 1/N$ (1), that is, data are sampled N times per second in each channel.

Based on the sampling frequency expressed in the formula (1), $$J_{start} = \text{Floor}(F_{min}/\Delta f) + 1 \quad (2),$$

where Floor means rounding down, $$J_{end} = \text{Floor}(F_{max}/\Delta f) + 1 \quad (3)$$

and J terms may be obtained through division based on the respiratory frequency range:

$$J = J_{end} - J_{start} + 1 \quad (4).$$

In step S124, a filter W is constructed based on phases of the plurality of respiratory frequency components.

The filter W which transforms the first time domain signals into the vector matrix including the representations of the phases is constructed. Alternatively, as understood, the filter W which is constructed by using the phases of the respiratory frequency components as a frequency band decomposes the first time domain signals into the plurality of respiratory frequency components and transforms the components into the vector matrix including the representations of the phases, that is, W: J*K, where the filter W is in the form of a matrix, and "*" represents multiplication;

suppose that $j = J_{start}, J_{start}+1, J_{start}+2, \ldots, J_{end}$; and $k=1, 2, \ldots, K$, where $K = T*N$. T is a time period selected in the first time domain signals, so as to further obtain the plurality of respiratory frequency components and the phases corresponding to the components described above. Elements in the matrix of the filter W may be expressed, based on the phases of the respiratory frequency components, as:

$$W(j-J_{start}+1,k)=\sin(2*pi*j*k/K) \quad (5)$$

$$W(j-J_{start}+1+J,k)=\cos(2*pi*j*k/K) \quad (5)$$

or each element is equivalently expressed as:

$$W(j,k) = e^{-\frac{2jk\pi i}{K}}, \quad (7)$$

where the phases of the plurality of respiratory frequency components may be expressed as $$e^{-\frac{2jk\pi i}{K}},$$

or a set of $$\left[e^{-\frac{2jk\pi i}{K}}\right]$$

represents the phases of the respiratory frequency components to obtain a basis or a basis set.

Here, the filter W may be understood as a band-pass filter obtained based on an a priori frequency band of the respiratory frequency. A matrix R represented by a set of row vectors is obtained by separately sampling the pilot tone signals S(t) in a time period T, where R=[S($t_0$); S($t_1$); . . . ; S($t_{T*N}$)]. The pilot tone signals S(t) are discretized, where a range of the time period T is [$t_0$, $t_T$].

In step S126, the first time domain signals are transformed based on the filter W into a vector matrix C including representations of phases.

Finally, here, each pilot tone signal S(t) is filtered, the matrix R represented by the set of row vectors that is obtained by sampling the foregoing pilot tone signals S(t) by the filter W is transformed into the vector matrix C including the representations of the phases, where the filter W may alternatively be referred to as a vector coefficient or a filter coefficient, and have corresponding phases $$e^{-\frac{2jk\pi i}{K}},$$

that is,

C=W*R (8), where a matrix J×M is obtained, M representing the number of channels receiving the pilot tone signals.

In step S130, an eigenvector is computed based on the vector matrix C including the representations of the phases that is obtained through transformation.

In order to compute, based on the vector matrix C, the eigenvector related to a respiratory movement or a non-respiratory body movement, eigendecomposition may be used, which may be expressed as:

$$[V,D]=eig(C'*C) \quad (9), \text{ or mathematically expressed as}$$

$$C'*C*V=V*D \quad (10)$$

where C' represents a conjugate transpose matrix of the vector matrix C, D represents a diagonal matrix composed of eigenvalues, and V represents the eigenvector. D and the eigenvector V may be computed through the formula (9) or (10).

In step S140, the first time domain signals S(t) are transformed into second time domain signals $S_{resp}(t)$ based on the eigenvector V, where the second time domain signals $S_{resp}(t)$ represent a characterization or representation of the acquired original time domain signals by using coordinates in a respiratory frequency space.

In a shown aspect, the eigenvector V is obtained based on the vector matrix C described above, that is, $$S_{resp}(t)=S(t)*V \quad (11)$$

where components related to the respiratory frequency or respiratory movement may be measured in the second time domain signals $S_{resp}(t)$. That is, it is easily understood that the components highly related to the respiratory frequency are amplified under the action of the eigenvector V by means of coordinate representation in the respiratory frequency space. Here, the eigenvector V may be arranged in ascending order.

In step S150, at least one maximum energy term related to the respiratory movement is removed from the second time domain signals $S_{resp}(t)$, the second time domain signals $S_{resp}(t)$ are divided up based on different sub-time periods, and a correlation coefficient between the second time domain signals $S_{resp}(t)$ in different sub-time periods is computed, to detect a non-respiratory body movement signal in the second time domain signals $S_{resp}(t)$.

Here, a window (function) with a certain width may be set to divide the second time domain signals $S_{resp}(t)$ up to obtain a plurality of sub-time periods, and the correlation coefficient between the second time domain signals $S_{resp}(t)$ in different sub-time periods is computed. For example, the correlation coefficient thereof is computed to detect the non-respiratory body movement signal therein.

Specifically, $S_{resp}(t)$ in a first window is selected and sampled to obtain a discrete matrix $R_1$. Similarly, $S_{resp}(t)$ in a second window with the same width is selected to obtain a matrix $R_2$. The correlation coefficient between the second time domain signals $S_{resp}(t)$ in sub-time periods in different windows is computed in a known manner. For example, $R_1$ and $R_2$ are separately normalized and then covariances and variances thereof are computed to compute a correlation coefficient therebetween.

In step S160, it is determined whether the correlation coefficient between corresponding second time domain signals $S_{resp}(t)$ in different sub-time periods is less than a threshold.

Here, the correlation coefficient between the corresponding second time domain signals $S_{resp}(t)$ in different sub-time periods is compared with an a priori threshold to determine whether the second time domain signals $S_{resp}(t)$ in different sub-time periods contain a movement signal introduced by the non-respiratory body movement or the non-mechanical physiological movement. That is, when the correlation coefficient is less than the threshold, it is detected that at least one second time domain signal $S_{resp}(t)$ contains the movement signal. When the correlation coefficient is greater than the threshold, it may be obviously determined that there is no portion of the non-respiratory body movement. Therefore, the original first time domain signal S(t) may be used as an indicator for execution of a sequence. For example, one or more time points for triggering acquisition of an MR signal in a time domain or an acquisition window is set, or the MR signal acquired in the time domain is subjected to post-processing. Referring to FIG. 8, by computing the correlation coefficient as described above, a portion 136 (represented by a triangle in the figure) of the non-respiratory body movement is detected in the first window 132, and the portion 136 of the non-respiratory body movement does not include respiratory movement signals including an irregular respiratory movement signal.

In step S170, in response to a comparison showing that the correlation coefficient is less than the threshold, the portion of the non-respiratory body movement in the second time domain signals $S_{resp}(t)$ is detected, which information is fed back to a control unit 126 in near real time to abort the execution of the sequence.

The control unit 126 receives the information that the non-respiratory body movement signal is detected, and is further configured to abort the execution of the sequence, including triggering, gating, etc. That is, the control unit 126 determines whether to abort setting of one or more time points for triggering acquisition of an MR signal in a time domain of the portion of the non-respiratory body movement or setting of an acquisition window, or to abort post-processing of the MR signal acquired in the time domain and related to the portion of the non-respiratory body movement. In addition, the post-processing of the acquired MR signal may include movement compensation, etc. to reduce an image artifact or blur. After the execution of the sequence is aborted, it is possible to return to step S110 and start to continuously detect pilot tone signals S(t) acquired in another time period.

In addition, in step S170, the pilot tone signals S(t) from a plurality of channels may be combined and displayed on a display unit 128. After step S170 is performed, it is possible to return to step S110, to perform the step of detecting movements, which may include a portion or component of a non-respiratory body movement, in a plurality of original first time domain signals or pilot tone signals S(t) acquired from the plurality of channels in a next time period.

In step S180, in response to a comparison showing that the correlation coefficient is greater than the threshold, the portion of the non-respiratory body movement in the second time domain signals $S_{resp}(t)$ is not detected, the first time domain signals from the plurality of channels are combined to obtain a curve of the respiratory movement signals, and the curve is used as an indicator (or marker) for execution of a sequence. In addition, alternatively, in step S170, the curve of the respiratory movement signals obtained by combining the pilot tone signals S (t) from the plurality of channels may be displayed on the display unit 128.

Figure 6:
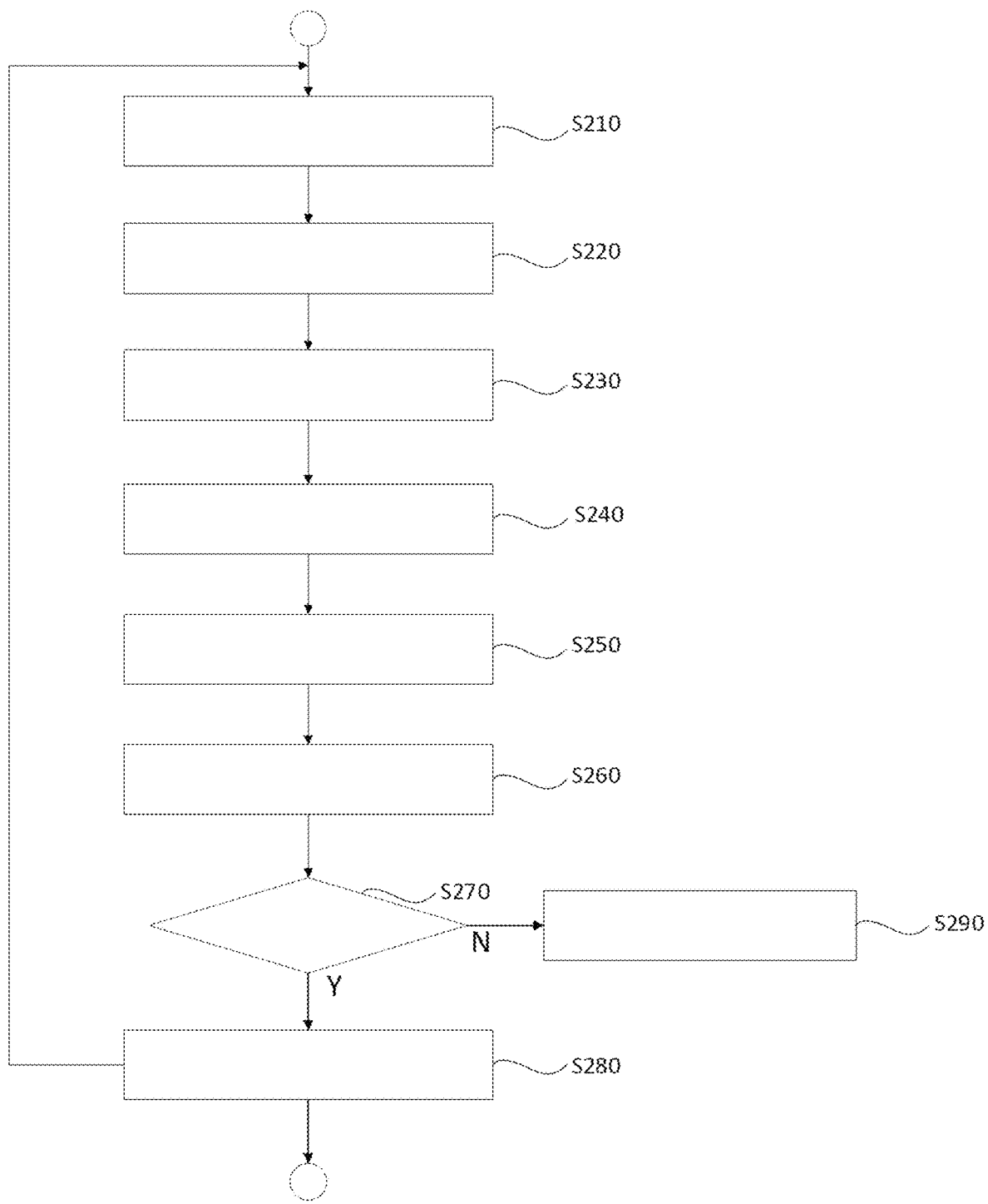
FIG. 6 is a flow chart of a medical imaging method for detecting a movement according to another exemplary aspect.

FIG. 6 shows another medical imaging method for detecting a movement. The method is intended to explicitly remove components related to a respiratory movement from a second time domain signal, where steps S210 to S240 may correspond to steps S110 to S140 illustrated in FIG. 5, respectively, and details are not described herein again.

In step S250, at least one maximum energy term is removed from the second time domain signals $S_{resp}(t)$, to obtain third time domain signals $S_{mo}(t)$ related to the non-respiratory movement components.

The last or largest columns of maximum energy terms, or maximum respiratory energy terms, in the second time domain signals $S_{resp}(t)$ obtained through transformation into a respiratory frequency space, that is, the maximum energy terms represented by, for example, the largest two columns of signals, correspond to the maximum respiratory energy. Usually, the last two columns of signals may be removed from the second time domain signals $S_{resp}(t)$, to further obtain the third time domain signals $S_{mo}(t)$ related to only the non-respiratory movement components.

In step S260, the third time domain signals $S_{mo}(t)$ are divided up based on different sub-time periods, and a correlation coefficient between the third time domain signals $S_{mo}(t)$ in different sub-time periods is computed, to detect a non-respiratory body movement signal in the third time domain signals $S_{mo}(t)$.

Here, a window (function) with a certain width may be set to divide the third time domain signals $S_{mo}(t)$ up to obtain a plurality of sub-time periods, and the correlation coefficient between the third time domain signal $S_{mo}(t)$ in different sub-time periods is computed. For example, the correlation coefficient thereof is computed to detect the non-respiratory body movement signal therein.

Specifically, $S_{mo}(t)$ in a first window is selected and sampled to obtain a discrete matrix $R_1$. Similarly, $S_{mo}(t)$ in a second window with the same width is selected to obtain a matrix $R_2$. The correlation coefficient between the third time domain signals $S_{mo}(t)$ in sub-time periods in different windows is computed in a known manner. For example, $R_1$ and $R_2$ are separately normalized and then covariances and variances thereof are computed to compute a correlation coefficient therebetween.

In step S270, it is determined whether the correlation coefficient between corresponding third time domain signals $S_{mo}(t)$ in different sub-time periods is less than a threshold.

Figure 9:
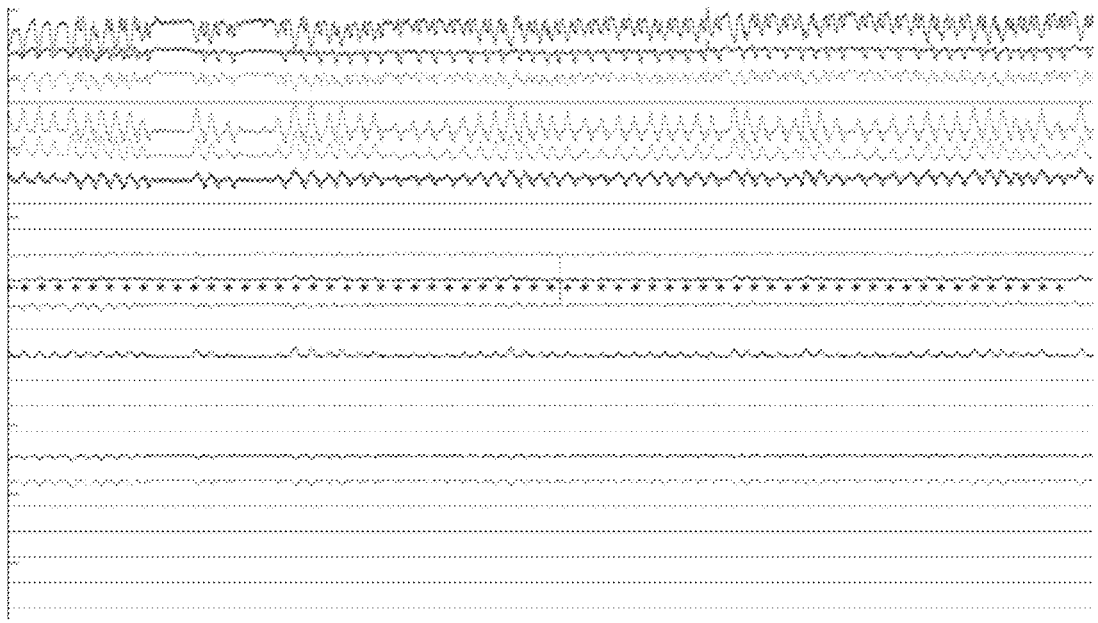
FIG. 9 is a schematic diagram of a time domain signal in which a respiratory movement is detected in pilot tone signals from a plurality of channels according to an exemplary aspect.

Here, the correlation coefficient between the corresponding third time domain signals $S_{mo}(t)$ in different sub-time periods is compared with an a priori threshold to determine whether the third time domain signals $S_{mo}(t)$ in different sub-time periods contain a movement signal introduced by a non-respiratory body movement or a non-mechanical physiological movement. That is, when the correlation coefficient is less than the threshold, it is detected that at least one of the third time domain signals $S_{mo}(t)$ contains the non-respiratory body movement signal. When the correlation coefficient is greater than the threshold, it may be obviously determined that there is no non-respiratory body movement signal in one $S_{mo}(t)$. Referring to FIG. 9, which shows that in a result of detecting the portion 136 of the non-respiratory body movement, the portion 136 of the non-respiratory body movement is not detected by using the method even in the presence of irregular respiratory signals, including deep/shallow respiration, breath holding, etc. showing robustness under certain interference.

In step S280, in response to the portion of the non-respiratory body movement being detected in the third time domain signals $S_{mo}(t)$, which information is fed back to a control unit 126 indicating that the portion of the non-respiratory body movement is detected in $S_{mo}(t)$ in near real time to abort execution of a sequence.

In step S290, in response to the portion of the non-respiratory body movement being not detected in the third time domain signals $S_{mo}(t)$, the first time domain signals S(t) from the plurality of channels are combined to obtain a curve of the respiratory movement signals, and the curve is used as an indicator (or marker) for execution of a sequence.

It should be noted that in addition to the magnetic resonance imaging system, the foregoing method for detecting a movement of an object under examination in medical imaging is also applicable to magnetic resonance imaging systems including computed tomography (CT), positron emission tomography (PET), single-photon emission computed tomography (SPECT), etc.

According to one aspect of the present disclosure, an electronic device is further provided, the electronic device including: a processor; and a memory storing a program, the program including instructions that, when executed by the processor, cause the processor to perform the foregoing medical imaging method for detecting a movement.

According to another aspect of the present disclosure, a computer-readable storage medium is further provided, storing a program, the program including instructions that, when executed by a processor of an electronic device, cause the electronic device to perform the foregoing medical imaging method for detecting a movement. The computer-readable storage medium includes a storage device, a floppy disk, a compact disk (CD), a digital versatile disk (DVD), a Blu-ray disk, a random access memory (RAM), or other storage devices containing instructions that cause a computer to perform the foregoing method.

Figure 10:
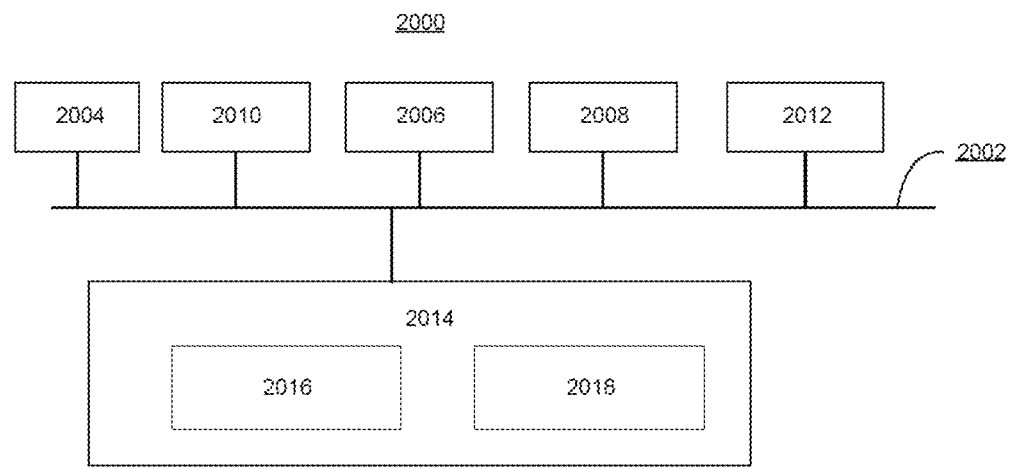
FIG. 10 is a structural diagram of a computing device applicable to an exemplary aspect.

Referring to FIG. 10, a computing device 2000 is now described, which is an example of an electronic device that may be applied to various aspects of the present disclosure. The computing device 2000 may be any machine configured to perform processing and/or computation, which may be, but is not limited to, a workstation, a server, a desktop computer, a laptop computer, a tablet computer, a personal digital assistant, a robot, a smartphone, an onboard computer, or any combination thereof. The foregoing medical imaging method for detecting a movement may be implemented, in whole or at least in part, by the computing device 2000 or a similar device or system.

The computing device 2000 may include elements in connection to a bus 2002 or in communication with a bus 2002 (possibly via one or more interfaces). For example, the computing device 2000 may include the bus 2002, one or more processors 2004, one or more input devices 2006, and one or more output devices 2008. The one or more processors 2004 may be any type of processors, and may include, but are not limited to, one or more general-purpose processors and/or one or more dedicated processors (for example, special processing chips). The input device 2006 may be any type of device capable of inputting information to the computing device 2000, and may include, but is not limited to, a mouse, a keyboard, a touch screen, a microphone, and/or a remote control. The output device 2008 may be any type of device capable of presenting information, and may include, but is not limited to, a display, a speaker, a video/audio output terminal, a vibrator, and/or a printer. The computing device 2000 may further include a non-transitory storage device 2010 or be connected to the non-transitory storage device 2010. The non-transitory storage device may be non-transitory and may be any storage device capable of implementing data storage, and may include, but is not limited to, a disk drive, an optical storage device, a solid-state memory, a floppy disk, a flexible disk, a hard disk, a magnetic tape, or any other magnetic medium, an optical disk or any other optical medium, a read-only memory (ROM), a random access memory (RAM), a cache memory and/or any other memory chip or cartridge, and/or any other medium from which a computer can read data, instructions and/or code. The non-transitory storage device 2010 can be removed from an interface. The non-transitory storage device 2010 may have data/programs (including instructions)/code for implementing the foregoing methods and steps. The computing device 2000 may further include a communication device 2012. The communication device 2012 may be any type of device or system that enables communication with an external device and/or network, and may include, but is not limited to, a modem, a network card, an infrared communication device, a wireless communication device and/or a chipset, e.g., a Bluetooth™ device, a 1302.11 device, a WiFi device, a WiMax device, a cellular communication device, and/or the like.

The computing device 2000 may further include a working memory 2014, which may be any type of working memory that may store programs (including instructions) and/or data useful to the working of the processor 2004, and may include, but is not limited to, a random access memory and/or read-only memory device.

Software elements (programs) may be located in the working memory 2014, and may include, but are not limited to, an operating system 2016, one or more application programs 2018, drivers, and/or other data and code. The instructions for performing the foregoing methods and steps may be included in the one or more application programs 2018. The foregoing medical imaging method for detecting a movement can be implemented by the processor 2004 by reading and executing instructions of the one or more application programs 2018. More specifically, in the foregoing medical imaging method for detecting a movement, steps 110 to 180, 210 to 290, and 122 to 126 may be implemented, for example, by the processor 2004 by executing the application programs 2018 having instructions for steps 110 to 180, 210 to 290, and 122 to 126. Moreover, other steps of the foregoing medical imaging method for detecting a movement may be implemented, for example, by the processor 2004 by executing the application programs 2018 having instructions for performing corresponding steps. Executable code or source code of the instructions of the software elements (programs) may be stored in a non-transitory computer-readable storage medium (for example, the foregoing storage device 2010), and may be stored in the working memory 2014 when executed (may be compiled and/or installed). The executable code or source code of the instructions of the software elements (programs) may alternatively be downloaded from a remote location.

It should further be appreciated that various variations may be made according to specific requirements. For example, tailored hardware may also be used, and/or specific elements may be implemented in hardware, software, firmware, middleware, microcode, hardware description languages, or any combination thereof. For example, some or all of the disclosed methods and devices may be implemented by programming hardware (for example, a programmable logic circuit including a field programmable gate array (FPGA) and/or a programmable logic array (PLA)) in an assembly language or a hardware programming language (such as VERILOG, VHDL, and C++) by using the logic and algorithm in accordance with the present disclosure.

It should be further understood that the foregoing methods may be implemented in a server-client mode. For example, the client may receive data input by a user and send the data to the server. Alternatively, the client may receive data input by the user, perform part of the processing in the foregoing method, and send data obtained after the processing to the server. The server may receive the data from the client, perform the foregoing method or another part of the foregoing method, and return an execution result to the client. The client may receive the execution result of the method from the server, and may present same to the user, for example, through an output device.

It should further be understood that the components of the computing device 2000 can be distributed over a network. For example, some processing may be executed by one processor while other processing may be executed by another processor away from the one processor. Other components of the computing system 2000 may also be similarly distributed. As such, the computing device 2000 can be interpreted as a distributed computing system that performs processing at a plurality of locations.

Although the aspects or examples of the present disclosure have been described with reference to the drawings, it should be appreciated that the methods, systems, and devices described above are merely exemplary aspects or examples, and the scope of the present disclosure is not limited by the aspects or examples, but only defined by the appended authorized claims and equivalent scopes thereof. Various elements in the aspects or examples may be omitted or substituted by equivalent elements thereof. Moreover, the steps may be performed in an order different from that described in the present disclosure. Further, various elements in the aspects or examples may be combined in various ways. It is important that, as the technology evolves, many elements described herein may be replaced with equivalent elements that appear after the present disclosure.

The invention claimed is:

1. A medical imaging method for detecting a movement, comprising:
   receiving, through a plurality of channels, a plurality of original first time domain signals recording a movement of an object under examination;
   transforming, based on a plurality of respiratory frequency components as bases, the plurality of original first time domain signals into a vector matrix comprising representations of phases;
   computing an eigenvector based on the vector matrix comprising the representations of the phases;
   transforming the first time domain signals into second time domain signals based on the eigenvector;
   removing at least one maximum energy term related to a respiratory movement from the second time domain signals, and determining whether a portion of a non-respiratory body movement in the second time domain signals is detected; and
   determining, after the portion of the non-respiratory body movement is detected, whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement.

2. The method as claimed in claim 1, wherein the removal of at least one maximum energy term related to a respiratory movement from the second time domain signals, and determining whether a portion of a non-respiratory body movement in the second time domain signals is detected comprises:
   removing at least one maximum energy term from the second time domain signals, to obtain third time domain signals, dividing the third time domain signals up based on different sub-time periods, and computing a correlation coefficient between the third time domain signals in the sub-time periods; and
   determining, based on a comparison between the correlation coefficient and an a priori threshold, whether a portion of a non-respiratory body movement in the third time domain signals is detected.

3. The method as claimed in claim 1, wherein the reception, through a plurality of channels, of a plurality of original first time domain signals recording a movement of an object under examination comprises:
   receiving, from a plurality of coil units through the plurality of channels, the plurality of original first time domain signals recording the movement of the object under examination, the first time domain signals comprising pilot tone signals or navigation echo signals.

4. The method as claimed in claim 1, wherein the reception, through a plurality of channels, of a plurality of original first time domain signals recording a movement of an object under examination comprises:
   sampling, based on a sampling frequency in a time period, the plurality of original first time domain signals to construct discrete representations of the first time domain signals.

5. The method as claimed in claim 1, wherein the transformation, based on a plurality of respiratory frequency components as bases, of the plurality of original first time domain signals into a vector matrix comprising representations of phases comprises:
   dividing based on an a priori respiratory frequency range, a sampling frequency, and a time period for acquiring the plurality of original first time domain signals, to obtain the plurality of respiratory frequency components;
   constructing a filter based on phases of the plurality of respiratory frequency components; and
   transforming, based on the filter, the first time domain signals into the vector matrix comprising the representations of the phases.

6. The method as claimed in claim 1, wherein the computing of an eigenvector based on the vector matrix comprising the representations of the phases comprises:
   computing the eigenvector through eigendecomposition and based on the vector matrix represented by using the respiratory frequency components.

7. A magnetic resonance imaging system for providing an image representation of an object under examination positioned in an examination space of the magnetic resonance imaging system, wherein
   the magnetic resonance imaging system is adapted to perform the medical imaging method for detecting a movement as claimed in claim 1.

8. An electronic device, comprising:
   a processor; and
   a non-transitory memory storing a program comprising instructions that, when executed by the processor, cause the processor to perform the medical imaging method for detecting a movement as claimed in claim 1.

9. A non-transitory computer-readable storage medium storing a program comprising instructions that, when executed by a processor of an electronic device, cause an electronic device to perform the medical imaging method for detecting a movement as claimed in claim 1.

10. A system for detecting a movement of an object under examination in medical imaging, wherein the system comprises:
   an interface portion configured to receive, through a plurality of channels, a plurality of original first time domain signals recording a movement of an object under examination;
   a filter configured to transform, based on a plurality of respiratory frequency components as bases, the plurality of original first time domain signals into a vector matrix comprising representations of phases;
   an eigenvector computing portion configured to compute an eigenvector based on the vector matrix comprising the representations of the phases; and
   a movement determination portion configured to transform the first time domain signals into second time domain signals in a respiratory frequency space based on the eigenvector, remove at least one maximum energy term related to a respiratory movement from the second time domain signals to obtain third time domain signals, and compute a correlation between the third time domain signals in sub-time periods, to detect a portion of a non-respiratory body movement in the third time domain signals.

11. The system as claimed in claim 10, wherein the filter is configured to:
divide based on an a priori respiratory frequency range, a sampling frequency, and a time period for acquiring the plurality of original first time domain signals, to obtain the plurality of respiratory frequency components;
be constructed based on phases of the plurality of respiratory frequency components; and
transform the first time domain signals into the vector matrix comprising the representations of the phases.

12. The system as claimed in claim 10, wherein the movement determination portion is further configured to divide the third time domain signals up based on different sub-time periods, compute a correlation coefficient between the third time domain signals in the sub-time periods, and determine, based on a comparison between the correlation coefficient and an a priori threshold, whether a portion of a non-respiratory body movement in the third time domain signals is detected.

13. The system as claimed in claim 10, wherein the movement determination portion is further configured to provide feedback to a controller as to whether the portion of the non-respiratory body movement in the third time domain signals is detected, and the controller is configured to determine, after receiving feedback that the portion of the non-respiratory body movement is detected, whether to abort setting of one or more time points for triggering acquisition of a magnetic resonance signal in a time domain related to the portion of the non-respiratory body movement or setting of an acquisition window, or to abort post-processing of an acquired magnetic resonance signal related to the portion of the non-respiratory body movement.

* * * * *